US011872257B2

(12) United States Patent
Simon O'Brien et al.

(10) Patent No.: US 11,872,257 B2
(45) Date of Patent: Jan. 16, 2024

(54) *SACCHAROMYCES BOULARDII* FOR THE TREATMENT OF MOOD DISORDERS

(71) Applicant: BIOCODEX, Gentilly (FR)

(72) Inventors: Emmanuelle Simon O'Brien, Lacroix-Saint-Ouen (FR); Marc Verleye, Remy (FR); Marie-Emmanuelle Le Guern, Compiegne (FR)

(73) Assignee: BIOCODEX, Gentilly (FR)

( * ) Notice: Subject to any disclaimer, the term of this patent is extended or adjusted under 35 U.S.C. 154(b) by 0 days.

(21) Appl. No.: 16/638,290

(22) PCT Filed: Aug. 10, 2018

(86) PCT No.: PCT/EP2018/071726
§ 371 (c)(1),
(2) Date: Feb. 11, 2020

(87) PCT Pub. No.: WO2019/030371
PCT Pub. Date: Feb. 14, 2019

(65) Prior Publication Data
US 2020/0179469 A1  Jun. 11, 2020

(30) Foreign Application Priority Data
Aug. 11, 2017 (EP) ..................................... 17306065

(51) Int. Cl.
| | |
|---|---|
| *A61K 36/064* | (2006.01) |
| *A61P 25/22* | (2006.01) |
| *A61P 25/24* | (2006.01) |
| *A61K 9/00* | (2006.01) |
| *A61K 9/19* | (2006.01) |

(52) U.S. Cl.
CPC .......... *A61K 36/064* (2013.01); *A61K 9/0053* (2013.01); *A61K 9/19* (2013.01); *A61P 25/22* (2018.01); *A61P 25/24* (2018.01)

(58) Field of Classification Search
CPC ...... A61K 9/0053; A61K 9/19; A61K 39/064; A61K 36/064; A61P 25/22; A61P 25/24; A61P 25/26; A61P 25/28; A61P 25/18
USPC ........ 424/9.1, 9.2, 93.5, 93.51, 234.1, 274.1
See application file for complete search history.

(56) References Cited

U.S. PATENT DOCUMENTS

| | | | |
|---|---|---|---|
| 2006/0140974 A1 | 6/2006 | Choe et al. | |
| 2011/0027348 A1* | 2/2011 | Feher | A61P 29/00 424/450 |
| 2011/0280837 A1* | 11/2011 | Bergonzelli | A61P 25/16 424/93.3 |
| 2013/0190400 A1 | 7/2013 | Chang et al. | |
| 2016/0206670 A1* | 7/2016 | Wieser | A61K 36/07 |

FOREIGN PATENT DOCUMENTS

| | | | | |
|---|---|---|---|---|
| EP | 2110028 A1 | 10/2009 | | |
| EP | 2438821 A1 | 4/2012 | | |
| EP | 3072518 A1 | 9/2016 | | |
| WO | 2012001640 A1 | 1/2012 | | |
| WO | WO2016/065419 A1 * | 5/2016 | ........... | A61K 35/747 |

OTHER PUBLICATIONS

2014, George F. Parker, "CSM-5 and Psychotic and Mood Disorders", in Journal of the American Academy of Psychiatry and the Law Online, 42(2):182-190, June.*
1994, Shepherd et al., Psychopharmacology, 116:56-64.*
1977, Porsolt et al., Act. Int. Pharmacodyn. Ther., 229:327-336.*
Lu et al. 2017 (Therapeutic effects of flupentixol and melitracen combined with *Saccharomyces boulardii* in patents with diarrhea-predominant irritable bowel syndrome; World Chinese Journal of Digestology 25(11):1031-1036). (Year: 2017).*
Hatoum et al. 2012 (Antimicrobial and probiotic properties of yeast: from fundamental to novel applications; Frontiers in Microbiology 3(421): 1-12) (Year: 2012).*
Forsythe et al. 2010 (Mood and gut feelings; Brain, Behavior, and Immunity; 24: 9-16) (Year: 2010).*
Czerucka et al. 2007 (Review article: yeast as probiotics—*Saccharomyces boulardii*; Alimentary Pharmacology & Therapeutics 26: 767-778) (Year: 2007).*
Fabiano et al., 2014 (Probiotics: current evidences and new perspectives; Italian Journal of Pediatrics 40 (Suppl1): A46) (Year: 2014).*
Buts et al., "Twenty-Five Years of Research on *Saccharomyces boulardii* Trophic Effects: Updates and Perspectives" Digestive Diseases and Sciences, Jan. 2009, vol. 54, No. 1, pp. 15-18.
Choi et al., "A Randomized, Double-blind, Placebo-controlled Multicenter Trial of *Saccharomyces boulardii* in Irritable Bowel Syndrome, Effect on Quality of Life," Clin. Gastroenterol, 45(8):679-683 (2011).
Focus Allergy Research Group®, Newsletter, Sep. (2009).
Watawana et al., "Health, Wellness, and Safety Aspects of the Consumption of Kombucha," Hindawi Publishing Corporation Journal of Chemistry, ID 591869 (2015).
Fernandez et al., "Human gut microbiota—A lifetime history: from birth to adulthood," Acta Gastroenterol. Latinoam, 46:375-382 (2016).
Dinan, "How the gut influences the brain: the intestinal microbiome as a new dimension for understanding mental health," European Neuropsychopharmacology, 26:S23-S24, abstract No. S.02.01 (2016).
Umbrella et al., "Microbiota and neurologic diseases: potential effects of probiotics," J. Transl. Med., 14:298 (2016).
Statement of Grounds of Opposition to European counterpart Patent No. EP 3664894 dated Jun. 24, 2022.
Braun et al., "Comparison of the elevated plus and elevated zero mazes in treated and untreated male Sprague-Dawley rats: effects of anxiolytic and anxiogenic agents," Pharmacol Biochem Behav, 97(3):406-15 (2011).

(Continued)

*Primary Examiner* — Mary Maille Lyons
(74) *Attorney, Agent, or Firm* — ARENTFOX SCHIFF LLP

(57) ABSTRACT

The present invention relates to *Saccharomyces boulardii* yeast cells, for use in the prevention or treatment of mood disorders, in a person.

19 Claims, 1 Drawing Sheet

(56) References Cited

OTHER PUBLICATIONS

Lu et al., "Therapeutic effects of flupentixol and melitracen combined with *Saccharomyces boulardii* in patients with diarrheapredominant irritable bowel syndrome," World Chinese Journal of Digestology, 25(11):1031-1036 (2017).

* cited by examiner

SACCHAROMYCES BOULARDII FOR THE TREATMENT OF MOOD DISORDERS

CROSS-REFERENCE TO RELATED APPLICATIONS

This application is a 371 National Stage Entry of PCT Application No. PCT/EP2018/071726, filed Aug. 10, 2018, which claims priority to European Application No. 17306065.8, filed Aug. 11, 2017, the disclosures of which are hereby incorporated by reference in their entireties.

FIELD OF THE INVENTION

The present invention relates to a medicinal product for the prevention or treatment of mood disorders in an individual, in particular for the prevention or treatment of depressive disorders or anxious or anxiety disorders.

TECHNICAL BACKGROUND

Anxiety disorders are a group of psychological and neurological problems that manifest themselves in several forms of abnormal or pathological fear and anxiety. The fifth edition of the Diagnostic and Statistical Manual of Mental Disorders (DSM-5™) and the $10^{th}$ revision of the International Classification of Diseases (ICD-10) of the World Health Organization (WHO) thus recognize a wide variety of anxiety disorders, such as separation anxiety, selective mutism, specific phobia, social phobia, panic disorder, agoraphobia, generalized anxiety disorder, substance/medication-induced anxiety disorder, and anxiety disorder due to another medical condition.

While the main approaches to combating these disorders remain behavioral therapy and anxiolytic or antidepressant drugs, in particular benzodiazepines such as diazepam (Valium®) or alprazolam (Xanax®), which currently constitute the reference pharmacological treatment, other approaches are also being explored in order to limit the side effects of the latter compounds.

For example, Desbonnet et al. (2010) Neuroscience 170: 1179-1188 showed that *Bifidobacterium infantis* 35624 decreased the depressive behaviors measured by the forced swimming test in the model of depression induced by maternal separation in rats. However, the efficacy of the probiotic is limited compared to the antidepressant used in this study, citalopram.

It is therefore still necessary to identify other alternatives to current anxiolytics with comparable efficacy to the latter.

*Saccharomyces boulardii*, also known as *Saccharomyces cerevisiae* var. *boulardii*, is a particular strain of the yeast *Saccharomyces cerevisiae*. This probiotic is mainly indicated as a complement to rehydration for the treatment of diarrhea. Its usefulness has been particularly established in children (Villarruel et al. (2007) *Acta Paediatr* 96:538-541; Szajewska et al. (2007) *Aliment Pharmacol Ther* 25:257-264) and for diarrhea related to antibiotic use (Surawicz et al. (1989) *Gastroenterology* 96:981-988; Kotowska et al. (2005) *Aliment Pharmacol Ther* 21:583-590) or to *Clostridium difficile* infections (Surawicz et al. (2000) *Clin Infect Dis* 31:1012-1017).

SUMMARY OF THE INVENTION

The present invention results from the unexpected discovery by the inventors that the administration of *Saccharomyces boulardii* yeast cells to mice reduced anxiety in these mice.

Thus, the present invention relates to *Saccharomyces boulardii* yeast cells for use:
  in the prevention or treatment of mood disorders in an individual, and/or
  in the prevention or treatment of depressive disorders or depression, or for use as an antidepressant, in an individual, and/or
  in the prevention or treatment of anxious or anxiety disorders, or for use as an anxiolytic, in an individual.

In a particular embodiment of the invention, the *Saccharomyces boulardii* yeast cells for use as defined above are in combination with at least one other substance intended for the prevention or treatment of mood disorders in an individual, in particular for the prevention or treatment of depressive disorders or depression, or of anxious or anxiety disorders.

The present invention also relates to a pharmaceutical composition or medicinal product comprising *Saccharomyces boulardii* yeast cells as active principle and optionally at least one pharmaceutically acceptable carrier or excipient, for use in the prevention or treatment of mood disorders in an individual, in particular in the prevention or treatment of depressive disorders or depression, or of anxious or anxiety disorders, or for use as an antidepressant or anxiolytic.

In a particular embodiment of the invention, the pharmaceutical composition or the medicinal product for use as defined above, comprises at least one other substance intended for the prevention or treatment of mood disorders in an individual, in particular for the prevention or treatment of depressive disorders or depression, or of anxious or anxiety disorders.

The present invention also relates to a method for the prevention or treatment of a mood disorder in an individual, in particular a method for the prevention or treatment of a depressive disorder or depression, or of an anxious or anxiety disorder in an individual, comprising administering to the individual an effective amount of *Saccharomyces boulardii* yeast cells.

In a particular embodiment of the method according to the invention, the yeast cells are in combination with at least one other substance intended for the prevention or treatment of mood disorders in an individual, in particular for the prevention or treatment of depressive disorders or depression, or of anxious or anxiety disorders.

The present invention also relates to the use of *Saccharomyces boulardii* yeast cells for the preparation of a medicinal product for the prevention or treatment of mood disorders in an individual, in particular for the prevention or treatment of depressive disorders or depression, or of anxious or anxiety disorders.

In a particular embodiment of the use as defined above of the invention, the medicinal product comprises at least one other substance intended for the prevention or treatment of mood disorders in an individual, in particular for the prevention or treatment of depressive disorders or depression, or of anxious or anxiety disorders.

The present invention also relates to a pharmaceutical composition or a medicinal product comprising as active substance:
  *Saccharomyces boulardii* yeast cells, and
  at least one other substance intended for the prevention or treatment of mood disorders in an individual, in particular the prevention or treatment of depressive disorders or depression, or of anxious or anxiety disorders,
optionally in combination with at least one pharmaceutically acceptable carrier or excipient.

The present invention also concerns products containing:
Saccharomyces boulardii yeast cells, and
at least one other substance intended for the prevention or treatment of mood disorders in an individual, in particular the prevention or treatment of depressive disorders or depression, or of anxious or anxiety disorders,
as a combination product for separate, simultaneous or sequential use for the prevention or treatment of mood disorders in an individual, in particular for the prevention or treatment of depressive disorders or depression, or of anxious or anxiety disorders, or for use as an antidepressant or anxiolytic.

DETAILED DESCRIPTION OF THE INVENTION

As a preliminary remark, it should be recalled that the term "comprising" means "including", "containing" or "encompassing", i.e., when an object "comprises" one or more elements, other elements than those mentioned may also be comprised in the object. In contrast, when an object "consists of" one or more elements, the object cannot comprise other elements than those mentioned.

Furthermore, as the skilled person will well understand, the expression "Substance or composition for use in the prevention or treatment of a disease" is synonymous with the expression "Substance or composition for use in a method for the prevention or treatment of a disease".

Mood Disorders

As used here, "the prevention or treatment" of mood disorders, in particular depressive disorders or depression, or anxious or anxiety disorders, is intended to therapeutically treat, to alleviate, or to prevent, in a prophylactic manner, mood disorders, in particular depressive disorders or depression, or anxious or anxiety disorders.

"Mood disorders" are well known to the skilled person and include in particular depressive disorders or depression and anxious or anxiety disorders. "Depressive disorders" are well known to the skilled person and are defined in the chapter "Depressive Disorders" on pages 155 to 188 of the fifth edition of the Diagnostic and Statistical Manual of Mental Disorders (5th edition, DSM-5™, 2013, American Psychiatric Association) and correspond in particular to the categories F20.4, F25.1, F31.3, F31.4, F31.5, F32, F33, F41.2, F92.0 of the Tenth Revision of the International Classification of Diseases Version 2016 (ICD-10: 2016).

Preferably, the depressive disorders according to the invention are substance/medication-induced depressive disorder, disruptive mood dysregulation disorder, major depression, persistent depressive disorder, depressive disorder due to another medical condition, as well as more generally any specified and unspecified depressive disorder.

"anxious disorders" and "anxiety disorders" are well known to the skilled person and are in particular defined in the chapter "Anxiety Disorders" on pages 189 to 233 of the fifth edition of the Diagnostic and Statistical Manual of Mental Disorders (5th edition, DSM-5™, 2013, American Psychiatric Association) and correspond in particular to the categories F06.4, F40, F41, F93 and F94 of the Tenth Revision of the International Classification of Diseases Version 2016 (ICD-10: 2016).

Preferably, the anxious or anxiety disorders according to the invention are separation anxiety, selective mutism, specific phobia, social phobia, panic disorder, agoraphobia, generalized anxiety disorder, substance/medication-induced anxiety disorder, and anxiety disorder due to another medical condition, as well as more generally any specified and unspecified anxiety disorder.

Yeast Cells

Saccharomyces boulardii, abbreviated S. boulardii, is a yeast well known to the skilled person. In particular, it is described in Hennequin et al. (2001) J. Clin. Microbiol. 39:551-559. As used here, the nomenclatures "Saccharomyces boulardii" and "Saccharomyces cerevisiae var. boulardii" (abbreviated to S. cerevisiae var. boulardii) are considered equivalent.

As used here, the expression "yeast cells" includes viable or dead yeast cells, whole or in the form of debris. Preferably, at least part of the Saccharomyces boulardii yeast cells according to the invention are viable, in particular viable and cultivable, and more preferably a majority of the Saccharomyces boulardii yeast cells according to the invention are viable, in particular viable and cultivable.

The viability of a yeast cell can in particular be determined by methylene blue staining and microscopic observation. The number of viable and cultivable cells, which defines vitality, can be estimated by determining the number of colony forming units (CFU) comprised in the sample.

By way of example, the number of CFU of yeast cells in a liquid sample comprising yeast can be determined by spreading a determined volume of the sample on a solid medium, for example agar, allowing the growth of yeast and incubating the solid medium for a time, for example 48 h, and at a temperature, for example 30° C., allowing the growth of yeast colonies. The number of colonies in relation to the volume spread on the solid medium is used to determine the number of CFU in the sample. A detailed protocol for the determination of CFU in accordance with the invention is described in particular in Toothaker & Elmer (1984) Antimicrobial Agents and Chemotherapy 26:552-556 in the paragraph "Assay for S. boulardii". Furthermore, when the yeast sample is in the form of a solid, for example a lyophilized powder, it is preferable to determine the number of CFU comprised in the sample after taking up a determined mass of the sample in an aqueous solution, in particular distilled water or a 0.9% NaCl solution at pH 7.

A "yeast" according to the invention is a fungus, preferably a unicellular fungus. The yeast cells according to the invention are of the species Saccharomyces boulardii. Saccharomyces boulardii is well known to the skilled person and is described in particular in Hennequin et al. (2001) J. Clin. Microbiol. 39:551-559.

In a particularly preferred manner, the Saccharomyces boulardii yeast cells according to the invention are obtained from the branded medicinal products Ultra-Levure®, Bioflor®, Codex®, Econorm®, Enflor®, Enteral®, Florastor®, Floratil®, Florestor®, Inteflora®, Perenterol®, Perenteryl®, Precosa®, Reflor®, Ultra-Levura®, or from deposits made at the American Type Culture Collection (ATCC, USA) under reference 74012 or at the Collection Nationale de Culture et de Microorganismes (CNCM, France) under reference I-745.

Preferably, also the Saccharomyces boulardii yeast cells according to the invention are lyophilized, such as the branded Saccharomyces boulardii yeast cells Ultra-Levure®, Bioflor®, Codex®, Econorm®, Enflor®, Enteral®, Florastor®, Floratil®, Florestor®, Inteflora®, Perenterol®, Perenteryl®, Precosa®, Reflor®, or Ultra-Levura®.

Advantageously, the viability and the vitality of yeast cells obtained from lyophilizates are superior to what can be obtained from other yeast cell preservation methods.

As understood here, "lyophilization" is a method of preservation in which yeast cells are frozen and then subjected to sublimation of the frozen water they contain to give a lyophilisate in the form of a dry yeast powder containing preferably less than 2% water and more preferably less than 1% water. Preferably, lyophilized yeast cells are obtained from yeast cell concentrates. Any type of yeast cell lyophilization method known to the skilled person can be used. However, yeast cells are preferably lyophilized according to the invention using the following lyophilization method:
- cultivate the yeast cells in a liquid nutrient medium until the cells reach a stationary phase;
- concentrate the cultured yeast cells and freeze the concentrate;
- lyophilize the concentrate.

The lyophilized *Saccharomyces boulardii* yeast cells are in a powder form.

Individual

The individual according to the invention is an animal, preferably a mammal, and more preferably a human. As will be clear to the skilled person, the individual according to the invention has a mood disorder according to the invention, in particular a depressive disorder or depression according to the invention or an anxious or anxiety disorder according to the invention, or is at risk of having a mood disorder according to the invention, in particular a depressive disorder or depression according to the invention or an anxious or anxiety disorder according to the invention, in other words, the individual according to the invention needs an antidepressant or anxiolytic treatment.

Other Substance

As used here, the expression "other substance for the prevention or treatment of a mood disorder, in particular the prevention or treatment of a depressive disorder or depression, or of an anxious or anxiety disorder" concerns in particular any compound or probiotic, other than *Saccharomyces boulardii* yeast cells, intended to treat, alleviate or prevent mood disorders, in particular depressive disorder or depression, or anxious or anxiety disorder. The substance is thus preferentially an antidepressant substance, also called an "antidepressant", or an anxiolytic substance, also called an "anxiolytic".

As used here, the term "antidepressant" or "antidepressive" concerns in particular any compound or probiotic, other than *Saccharomyces boulardii* yeast cells, intended to treat, alleviate or prevent depressive disorders.

As used here, the term "anxiolytic" concerns in particular any compound or probiotic, other than *Saccharomyces boulardii* yeast cells, intended to treat, alleviate or prevent anxious or anxiety disorder.

As used here, the term "probiotic" refers to any microorganism, preferably a viable one, administered to an individual, in particular to improve the individual's health.

Preferably, the other substance intended for the prevention or treatment of a mood disorder, in particular the prevention or treatment of a depressive disorder or depression, or of an anxious or anxiety disorder, is selected from the group consisting of:
- a benzodiazepine, such as bromazepam, clobazam, prazepam, lorazepam, dipotassium clorazepate, clotiazepam, ethyl loflazepate, oxazepam, diazepam, alprazolam, or clonazepam;
- a selective serotonin reuptake inhibitor, such as citalopram, escitalopram, fluoxetine, fluvoxamine, sertraline, or paroxetine;
- a monoamine oxidase (MOA) inhibitor, such as moclobemide or iproniazid;
- a serotonin and catecholamine reuptake inhibitor, in particular norepinephrine, such as duloxetine, venlafaxine, milnacipran, imipramine, amitriptyline, clomipramine, dosulepine, doxepine, mirtazapine, or mianserin; or
- etifoxin, hydroxyzine, buspirone, tianeptin, aglomelatin, or captodiame.

Furthermore, in a particular embodiment of the invention, the *Saccharomyces boulardii* yeast cells according to the invention are not administered with another anxiolytic or antidepressant substance, or intended for the prevention or treatment of a mood disorder, in particular for the prevention or treatment of a depressive disorder or depression, or of an anxious or anxiety disorder, and the pharmaceutical composition, the medicinal product or the products according to the invention do not include any other anxiolytic or antidepressant substance, or substance for the prevention or treatment of a mood disorder, in particular for the prevention or treatment of a depressive disorder or depression, or of an anxious or anxiety disorder, other than the *Saccharomyces boulardii* yeast cells according to the invention.

In another particular embodiment of the invention, the *Saccharomyces boulardii* yeast cells are not administered with another probiotic, and the pharmaceutical composition, the medicinal product or the products according to the invention do not include a probiotic other than *Saccharomyces boulardii*.

In yet another particular embodiment of the invention, the *Saccharomyces boulardii* yeast cells are not administered with orotic acid or a salt thereof, or with *Bifidobacterium longum*, in particular *Bifidobacterium longum* ATCC BAA-999, and the pharmaceutical composition, the medicinal product or the products according to the invention do not include orotic acid or a salt thereof, or *Bifidobacterium longum*, in particular *Bifidobacterium longum* ATCC BAA-999.

Administration

Preferably, the *Saccharomyces boulardii* yeast cells, the pharmaceutical composition, the medicinal product and the products according to the invention are in a form suitable for oral administration. Thus, the *Saccharomyces boulardii* yeast cells, the pharmaceutical composition, the medicinal product and the products according to the invention are, or appear, preferably in the form of capsules or sachets of powder.

Preferably also, the *Saccharomyces boulardii* yeast cells according to the invention are administered at a dose of $0.5 \cdot 10^8$ to $100 \cdot 10^{10}$ CFU/kg/day or at a dose of 0.00125 g/kg/day to 25 g/kg/day.

Preferably also, the *Saccharomyces boulardii* yeast cells according to the invention are administered at a dose of 0.5 g/kg to 10 g/kg, more preferably at a dose of 1 to 6 g/kg and even more preferably at a dose of about 3 g/kg, in particular 1, 2, 3, 4 or 5 times a day.

As the skilled person will understand, the amount of yeast cells to be administered per unit of mass (kg) refers to the mass of the individual for whom the yeast cells are intended.

Furthermore, when the amount of yeast cells to be administered is expressed in units of mass (g), the yeast cells are preferably in lyophilized form.

Preferably, the pharmaceutical composition, the medicinal product or the products according to the invention, comprise the *Saccharomyces boulardii* yeast cells in a dose of 50 mg to 250 mg. Furthermore, the *Saccharomyces boulardii* yeast cells for use as defined above are preferably administered at a unit dose of 50 mg to 250 mg.

As used here, the expression "in combination" or "combination product" means that (i) the *Saccharomyces boulardii* yeast cells according to the invention and (ii) the other substance for the prevention or treatment of a mood disorder, in particular the prevention or treatment of a depressive disorder or depression, or of an anxious or anxiety disorder according to the invention may be combined within the same pharmaceutical composition or the same medicinal product, and thus be administered together, or be administered separately, i.e., according to separate routes of administration and/or separate administration regimes, provided that when they are administered separately the respective periods of anti-mood disorder activity of the *Saccharomyces boulardii* yeast cells and the other substance overlap in whole or in part, in particular so that they can cooperate to exert a synergistic anti-mood disorder effect.

The invention will be further explained in a non-limiting manner using the following figures and examples.

EXAMPLES

Example 1

Figure 1:
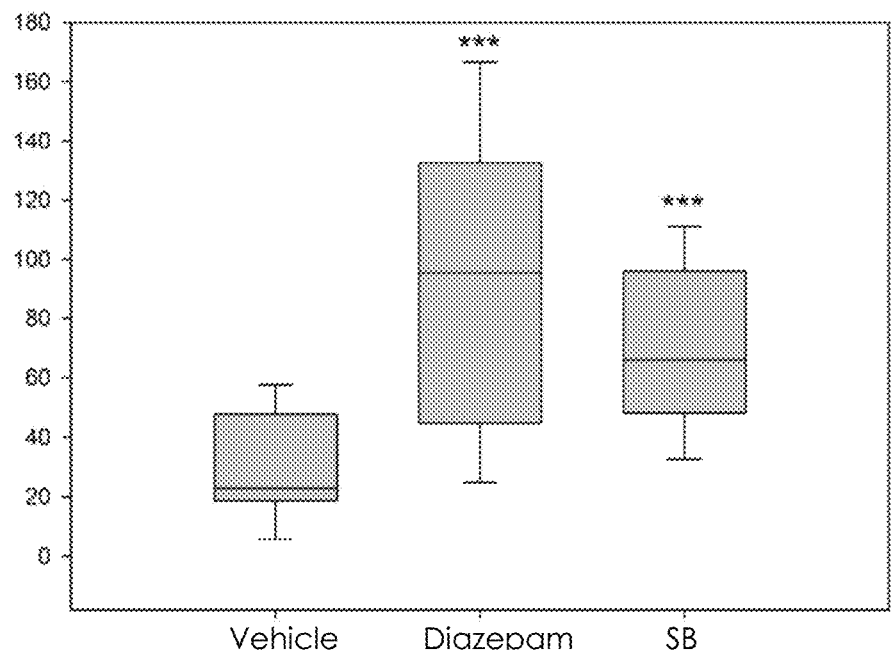
FIG. 1 shows a box diagram of the time spent (in seconds) in the open quadrants (vertical axis) by control mice (vehicle, =20), by diazepam-treated mice (diazepam, n=10) and by mice treated with *Saccharomyces boulardii* yeast cells (SB, n=10). Mice treated with SB (3 g/kg, p.o.) for 12 days or with a single administration of diazepam (1 mg/kg, i.p.) spent significantly more time in the open quadrants than control mice. A Kruskal-Wallis one-factor ANOVA was performed followed by Dunn's test. The three-star symbol (\*\*\*) represents p<0.05.

The inventors evaluated the effects of chronic treatment with *Saccharomyces boulardii* (SB) on the basal anxiety behavior of CD1 mice in the animal model of anxiety known as the elevated zero-maze initially described by Shepherd et al. (1994) *Psychopharmacology* (Berl). 116:56-64 and then taken up by others (see for example Kulkarni et al. (2007) *Methods Find Exp Clin Pharmacol*. 29:343-348 and Braun et al. (2011) *Pharmacol. Biochem. Behav.* 97:406-415).

1. Materials and Methods
1.1. Animals

Adult male CD1 mice (Charles River breeding) aged 7 weeks and weighing between 27 and 37 grams at the time of arrival are used after acclimatization for at least 1 week in the animal housing facility. The housing conditions are as follows: ambient t°=22±2° C.; Safe "A04" food, tap water as drinking water, light/dark cycle: 12 h/12 h (light: 7 h/19 h-dark: 19 h/7 h). The mice are housed at 10 per cage in 1500 U type cages. The experiments are carried out according to European recommendations (Directive 2010/63/EU) for the use of laboratory animals and have been validated and approved by the ethics committee (project number 2200.01).

1.2 Treatment

A group of mice (n=10) received lyophilized *Saccharomyces boulardii* (SB) CNCM 1-745 yeast cells (lot 9289 with a vitality of $31 \times 10^9$ CFU/g) solubilized in tap water, orally at a dose of 3 g/kg and with a volume of 10 ml/kg, twice daily for 12 days (from 9:30 to 10:30 and from 15:30 to 16:30). A second group of mice (n=10) received diazepam (Valium®, Roche, lot F1081F01), a reference anxiolytic, at a dose of 1 mg/kg intraperitoneally (i.p.) with a volume of 10 mL/kg, 30 minutes prior to the behavioral test. The control group (n=10) corresponding to the SB treatment received the liquid vehicle alone (water) at the same frequency and with the same route of administration as the treated animals. The diazepam treatment control group (n=10) received the liquid vehicle (0.9% NaCl) at the same frequency and with the same route of administration as the treated animals. Since the results of the 2 control groups were not significantly different, their results were combined to clarify the graphs.

1.3. Protocol

The elevated zero-maze consists of a round platform (2 open and 2 closed quadrants) 50 cm in diameter and 5 cm wide located 40 cm above the ground. A 15 cm high opaque wall delimits the closed quadrants and a 3 mm ledge surrounds the open areas. The brightness was 30 lux in the open areas and 3 lux in the closed areas. Animal movements are detected by means of an infrared floor and are analyzed by VideoTrack V2.5 software (ViewPoint). After a period of at least 45 minutes of habituation, the test begins when the animal is placed in the center of a closed quadrant, and lasts 5 minutes.

Entry into a new quadrant is considered when the animal rests all four legs in the area. The parameters measured are: time spent and percentage of time spent in open quadrants. Higher levels of anxiety are normally associated with less time spent in the open quadrants (more anxiety-provoking areas), resulting in less exploratory activity.

1.4. Statistical Analysis

The results are expressed as the mean±SEM. The results are analyzed using a one-factor Kruskal-Wallis analysis of variance (ANOVA) [treatment]. In the event of a statistically significant result, a multiple comparison test (Dunn) is carried out between the groups to determine those that differ at the 5% threshold (SigmaStat, V3.5, Systat Software Inc.).

2. Results

Figure 2:
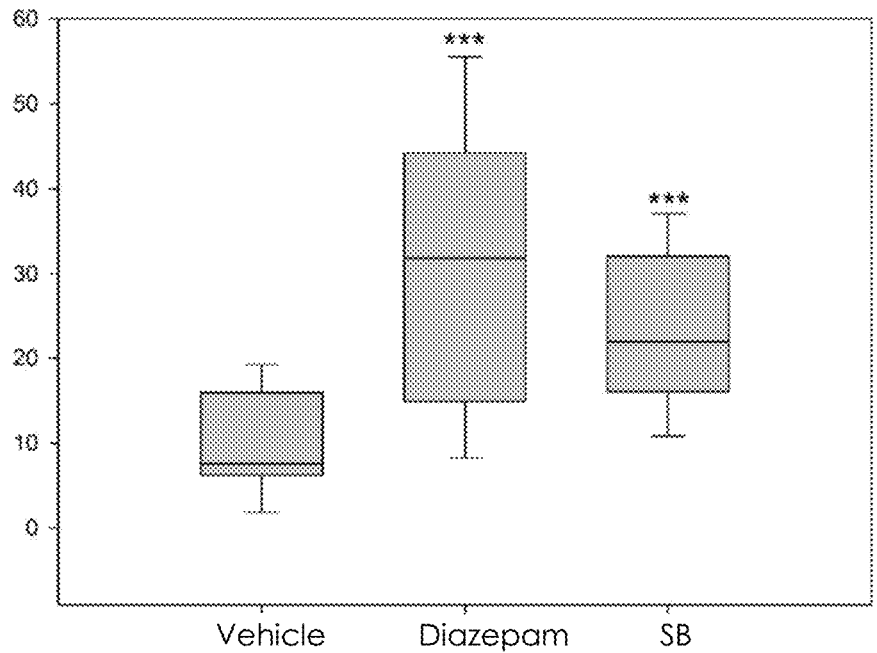
FIG. 2 shows a box diagram of the percentage of time spent in the open quadrants (vertical axis) by control mice (vehicle, n=20), by diazepam-treated mice (diazepam, n=10) and by mice treated with *Saccharomyces boulardii* yeast cells (SB, n=10). Mice treated with SB (3 g/kg, p.o.) for 12 days or with a single administration of diazepam (1 mg/kg, i.p.) spent significantly more time in the open quadrants than control mice. A Kruskal-Wallis one-factor ANOVA was performed followed by Dunn's test. The three-star symbol (\*\*\*) represents p<0.05.

The results of the experiment show that mice treated with *Saccharomyces boulardii* (SB) yeast cells twice daily for 12 days spent significantly more time in the open quadrants than control mice (71.6 sec for SB-treated mice versus 31.2 sec for control mice, or 23.9% versus 10.4% of the time) (p<0.05). Mice treated with diazepam, the reference anxiolytic, also spent significantly more time in the open quadrants compared with controls (91.9 sec or 30.6% of the time for diazepam-treated mice) (p<0.05) (FIGS. 1 and 2).

Conclusion

The results of this study show that chronic 2-week treatment with *Saccharomyces boulardii* in male CD1 mice significantly increased the time spent in the open quadrants of the elevated zero-maze in the same way as diazepam administration. These results demonstrate a beneficial effect of the yeast *Saccharomyces boulardii* on anxiety.

Example 2

The antidepressant effects of the yeast *Saccharomyces boulardii* are evaluated by chronic administration to adult male CD1 mice in the forced swimming test.

The forced-swimming test, well known to the skilled person, is used to measure the antidepressant effects of a pharmacological compound. This test is based on the work of Porsolt et al. (1977) *Act. Int. Pharmacodyn. Ther.* 229: 327-336 and has since been classically used to predict the clinical efficacy of antidepressant compounds.

Briefly, this test takes place in a cylindrical container filled with water (water height 10 cm) at 23° C. The mouse is placed in this container for 6 minutes, and the duration of immobility of the animal is measured for the last 4 minutes.

The antidepressant compounds administered prior to this test significantly reduce the immobility time of the animals.

The invention claimed is:

1. A method for treating mood disorders in an individual in need thereof comprising
    selecting an individual having a mood disorder, wherein the mood disorder is a depressive disorder, depression, an anxious disorder, or an anxiety disorder; and
    administering an effective amount of *Saccharomyces boulardii* yeast cells to said individual, wherein *Saccharomyces boulardii* yeast cells are not administered with another anxiolytic or antidepressant substance or with *Bifidobacterium longum*, and where a majority of the *Saccharomyces boulardii* yeast cells are viable.

2. The method of claim 1, wherein the *Saccharomyces boulardii* yeast cells are lyophilized.

3. The method of claim 1, wherein the *Saccharomyces boulardii* yeast cells are in a form suitable for an oral administration.

4. The method of claim 1, wherein the *Saccharomyces boulardii* yeast cells are in a form of capsules or sachets of powder.

5. The method of claim 1, wherein the *Saccharomyces boulardii* yeast cells are administered at a dose of 0.00125 to 25 g/kg/day.

6. The method of claim 1, wherein the depressive disorder is a substance/medication-induced depressive disorder, disruptive mood dysregulation disorder, major depression, persistent depressive disorder, or depressive disorder due to another medical condition.

7. The method of claim 1, wherein the anxious or anxiety disorder is separation anxiety, selective mutism, specific phobia, social phobia, panic disorder, agoraphobia, generalized anxiety disorder, substance/medication-induced anxiety disorder, or an anxiety disorder due to another medical condition.

8. A method for treating mood disorders in an individual in need thereof comprising
    selecting an individual having a mood disorder, wherein the mood disorder is a depressive disorder, depression, an anxious disorder, or an anxiety disorder; and
    administering an effective amount of a pharmaceutical composition or medicinal product comprising *Saccharomyces boulardii* yeast cells and at least one pharmaceutically acceptable carrier or excipient to said individual, wherein *Saccharomyces boulardii* yeast cells are not administered with another anxiolytic or antidepressant substance or with *Bifidobacterium longum*, and wherein a majority of the *Saccharomyces boulardii* yeast cells are viable.

9. The method of claim 8, wherein the *Saccharomyces boulardii* yeast cells are lyophilized.

10. The method of claim 8, wherein the composition or medicinal product is in a form suitable for an oral administration.

11. The method of claim 8, wherein the composition or product is in a form of capsules or sachets of powder.

12. The method of claim 8, wherein the composition or medicinal product comprises *Saccharomyces boulardii* yeast cells in a unit dose of 50 to 250 mg.

13. The method of claim 1, wherein the depressive disorder is a specified depressive disorder or an unspecified depressive disorder.

14. The method of claim 1, wherein the anxious or anxiety disorder is a specified or unspecified anxiety disorder.

15. A method for treating mood disorders in an individual in need thereof comprising
    selecting an individual having a mood disorder, wherein the mood disorder is a depressive disorder or a depression; and
    administering an effective amount of *Saccharomyces boulardii* yeast cells to said individual, wherein *Saccharomyces boulardii* yeast cells are not administered with another anxiolytic or antidepressant substance or with *Bifidobacterium longum*, and where a majority of the *Saccharomyces boulardii* yeast cells are viable.

16. The method of claim 15, wherein the *Saccharomyces boulardii* yeast cells are lyophilized.

17. The method of claim 15, wherein the *Saccharomyces boulardii* yeast cells are in a form suitable for an oral administration.

18. The method of claim 15, wherein the *Saccharomyces boulardii* yeast cells are in a form of capsules or sachets of powder.

19. The method of claim 15, wherein the *Saccharomyces boulardii* yeast cells are administered at a dose of 0.00125 to 25 g/kg/day.

* * * * *